(12) United States Patent
Hodges

(10) Patent No.: US 7,803,627 B2
(45) Date of Patent: Sep. 28, 2010

(54) PROCESS FOR EVALUATING QUALITY OF COKE AND BITUMEN OF REFINERY FEEDSTOCKS

(75) Inventor: Michael Graham Hodges, Surrey (GB)

(73) Assignee: BP Oil International Limited, Middlesex (GB)

( * ) Notice: Subject to any disclaimer, the term of this patent is extended or adjusted under 35 U.S.C. 154(b) by 192 days.

(21) Appl. No.: 11/922,245

(22) PCT Filed: Jun. 13, 2006

(86) PCT No.: PCT/GB2006/002164

§ 371 (c)(1),
(2), (4) Date: Dec. 14, 2007

(87) PCT Pub. No.: WO2006/136788

PCT Pub. Date: Dec. 28, 2006

(65) Prior Publication Data

US 2009/0117659 A1    May 7, 2009

(30) Foreign Application Priority Data

Jun. 23, 2005    (EP) .................................. 05253891

(51) Int. Cl.
*G01N 33/26* (2006.01)
(52) U.S. Cl. ......................... 436/60; 436/155; 436/157; 436/139; 436/145; 208/131

(58) Field of Classification Search ................... 436/60, 436/155, 157, 139, 145; 208/185, 357, 366, 208/131
See application file for complete search history.

(56) References Cited

U.S. PATENT DOCUMENTS

| 5,024,752 A | 6/1991 | Yan |
| 5,711,870 A | 1/1998 | Storm et al. |
| 2003/0141613 A1 | 7/2003 | Hajduk et al. |
| 2008/0248967 A1* | 10/2008 | Butler et al. .................. 506/12 |

OTHER PUBLICATIONS

International Search Report mailed Aug. 29, 2006.
Written Opinion of the International Searching Authority mailed Aug. 29, 2006.

* cited by examiner

*Primary Examiner*—Robert J Hill, Jr.
*Assistant Examiner*—Dwan A Gerido
(74) *Attorney, Agent, or Firm*—Nixon & Vanderhye

(57) ABSTRACT

Process for evaluating the coke and/or bitumen yield and quality of a plurality of refinery feedstocks, by (i) providing a plurality of refinery feedstocks, (ii) placing a sample of each of the plurality of refinery feedstocks on a heating device, (iii) heating each sample under vacuum to a temperature in the range 300° C. to 420° C. using the respective heating device while measuring the weight loss of the sample, and then (iv) (a) measuring the bitumen quality of the vacuum residues formed, and/or (b)(i) heating the vacuum residues to a temperature in the range 450° C. to 600° C. using the heating device, while measuring the weight loss of the sample, and then (ii) measuring the coke quality of the products formed.

11 Claims, No Drawings

PROCESS FOR EVALUATING QUALITY OF COKE AND BITUMEN OF REFINERY FEEDSTOCKS

This application is the U.S. national phase of International Application No. PCT/GB2006/002164 filed 13 Jun. 2006, which designated the U.S. and claims priority to EP 05253891.5 filed 23 Jun. 2005, the entire contents of each of which are hereby incorporated by reference.

This invention relates to processes for the evaluation of the coke and/or bitumen quality of a plurality of refinery feedstocks using high throughput experimentation.

Over recent years, a number of high throughput experimentation techniques have been developed to allow significant increases in the ability to synthesize and test catalytic and other materials for useful properties. In general, such techniques have focussed on development of apparatus and methodologies, including the growing use of robots and computers to design experiments and to automate catalyst and materials preparation and testing, to allow rapid and reproducible testing results to be achieved on relatively small scale samples. For example, much effort has gone in to developing preparation and testing apparatus for numerous types of materials and material properties (such as described in U.S. Pat. No. 5,776,359) and for chemical reactions of interest (such as described in U.S. Pat. Nos. 5,959,297, 6,063,633 and 6,306,658).

The high throughput technologies have generally focussed on discovery of new catalysts and materials for existing processes. We have now developed high throughput methodologies that can be applied to screening of refinery feedstocks to evaluate the coke and/or bitumen quality.

Bitumen (also known as asphalt) is a non-crystalline, viscous material that can be derived from refinery processing of crude oils. Bitumen has numerous uses, including, for example, in road construction and in roofing. Bitumen can have a number of different qualities, such as stiffness and viscosity, and these qualities can be strongly dependent on the type of crude oil processed and various processing steps employed during its production. Conventional methods for measuring the properties of Bitumen are described in British Standard (B.S.) 2000 "Methods of test for petroleum and its products", and, in particular, for example, in Part 49 "Penetration of bitumen and bituminous materials", Part 58 "Softening point of bitumen" and Part 72 "Viscosity of cutback bitumen".

Coke is formed from the residual carbon in a crude oil, and is typically produced by cracking of vacuum residue in a delayed coker process. Other types of cokers are available, such as a fluid coker or a flexicoker. They are thermal processes that crack the vacuum residue to lighter products and a petroleum coke. The coke formed in the delayed coker (green coke, but may also be called petroleum coke or raw petroleum coke) may be calcined to produce calcine petroleum coke, which, depending on its quality may be used for a number of processes, including to form carbon anodes for the aluminium industry and graphite electrodes for arc furnaces or titanium dioxide production. Coke can have a number of different qualities, dependent on the structure of the coke formed and on the impurities therein, and these qualities can be strongly dependent on the type of crude oil processed and various processing steps employed during its production.

Thus, the potential value of a crude oil is dependent on the quality and yield of the bitumen and/or coke, and any liquid products from the coking process, that may be produced in refining. On a typical refinery, a number of different refinery feedstocks are processed, such as a number of different crude oils. The refinery feedstocks are also usually blends of available feeds, and thus, it is very difficult to predict the bitumen or coke quality of the feedstock. Typically, a number of assumptions are made on the basis of previous operating experience, but these can usually only provide an approximate prediction.

The present invention seeks to evaluate the coke and/or bitumen yield and quality of refinery feedstocks in a high throughput manner.

Thus, according to the present invention there is provided a process for evaluating the coke and/or bitumen yield and quality of a plurality of refinery feedstocks, said process comprising*
(i) providing a plurality of refinery feedstocks,
(ii) placing a sample of each of said plurality of refinery feedstocks on a heating device, and
(iii) heating each sample under vacuum to a temperature in the range 300° C. to 420° C. using the respective heating device whilst measuring the weight loss
(iv) of the sample, and then
(v) (a) measuring the bitumen quality of the vacuum residues formed, and/or
(b) (i) heating the vacuum residues to a temperature in the range 450° C. to 600° C. using the heating device, whilst measuring the weight loss of the sample, and then
(ii) measuring the coke quality of the products formed.

The present invention provides a process for the evaluation of the coke and/or bitumen quality of a plurality of refinery feedstocks and hence allows the potential value of a refinery feedstock to be evaluated prior to its use, and potentially even before its purchase. The present invention also allows blends of feeds to be rapidly evaluated, allowing potential synergies from feed compatibilities (and potential incompatibilities) to be measured. For example, two or more refinery feedstocks such as two crude oils, or a crude oil and a synthetic crude, can be readily blended indifferent proportions to generate a plurality of potential refinery feedstocks for evaluation in the present invention. Where this is the case, blending is preferably performed using a suitable liquid handling robot.

Typically, the plurality of refinery feedstocks will comprise at least 20 refinery feedstocks, such as at least 50 refinery feedstocks.

The refinery feedstocks in step (i) may be any suitable refinery feedstocks, including crude oils, synthetic crudes, biocomponents, visbreaker tars, solvent deasphalted pitches, atmospheric residues, vacuum residues, fuel oils, FCC decant oils, and blends of one or more of said components, such as blends of one or more crude oils or blends of one or more crude oils with one or more synthetic crudes.

The heating devices may be any suitable devices which can be utilised to heat the samples to the required temperatures whilst simultaneously measuring the weight loss of the samples.

Suitable heating devices include optical devices and microoscillators, such as quartz microoscillators, as described in U.S. Pat. No. 5,661,233, or microthermal balances, as used for TGA measurements.

Preferably the devices are disposable.

The weight losses allow the determination of the relative amount (yield) of bitumen and/or coke compared to other components in the refinery feedstock as described further below.

In step (iii) of the process of the present invention, each sample is heated under vacuum to a temperature in the range 300° C. to 420° C. whilst measuring the weight loss of the sample. Heating under vacuum to a temperature in the range 300° C. to 420° C. causes the evolution of lower boiling components from the sample to leave the higher boiling components (vacuum residue), and it is the weight loss associated with these lower boiling components that is thus measured.

By "under vacuum" is meant at a pressure below atmospheric pressure, typically a pressure from below atmospheric (approximately 1 bar) to 1 mbar.

Each sample may be heated to the same temperature or samples may be heated to different temperatures to each other.

Preferably, each sample is heated under vacuum to a temperature in the range 320 to 400° C.

The sample may be heated initially at atmospheric pressure and then under vacuum, depending on the feedstock to be evaluated similar to the processes of atmospheric distillation and vacuum distillation conventionally applied on a refinery.

Other components, such as steam, may also be blended or otherwise provided before or during the heating in step (iii).

In a preferred embodiment, after heating under vacuum to a temperature in the range 300° C. to 420° C. whilst measuring the weight loss of the sample in step (iii), the vacuum residue formed may be blended with one or more other residues prior to any subsequent steps, said step also being similar to blending processes conventionally applied on a refinery.

For example, when the bitumen quality of the vacuum residue is to be measured (step (iv)(a)), the vacuum residue formed in step (iii) may be blended with one or more further vacuum resides (including blown vacuum residues as described further below) prior to determination of the bitumen quality.

Similarly, when the coke quality of the vacuum residue is to be measured (step (iv)(b)), the vacuum residue formed in step (iii) may be blended with one or more further residues, for example, with a vacuum residue, a solvent deasphalted pitch or a visbroken tar, prior to subsequent heating and measurement of the coke quality.

Similarly, where the refinery feedstock is initially heated at atmospheric pressure prior to heating under vacuum in step (iii), the residue formed after heating at atmospheric pressure (atmospheric residue) may be blended with one or more or more other residues prior to the subsequent heating under vacuum, for example with one or more further atmospheric residues.

In step (iv) of the process of the present invention the bitumen quality of the vacuum residues formed in step (iii) are measured and/or the vacuum residues are further heated and the coke quality measured.

As used herein, reference to subsequent measurement on and/or treatment of the vacuum residues includes reference to vacuum residues that have been blended with one or more further residues prior to said subsequent treatment as described above. In step (iv)(a) of the process of the present invention the bitumen quality of the vacuum residue obtained is measured.

A number of techniques may be used which can give information on the bitumen quality. Suitable analytical techniques include, for example, NMR and other spectroscopic techniques, preferred techniques being NIR and FTIR. The bitumen quality may also be measured using rheological and other techniques that correlate with the conventional empirical tests for bitumen quality. Suitable high throughput techniques for measurement of rheological and other physical properties include those described in, for example, WO 03/021232, WO 03/019150, US 2003/141613 and US 2004/123650.

The measurements may comprise measurements on the vacuum residue itself (i.e. without further treatment), such as analysis for sulphur content and/or viscosity of the vacuum reside. The sulphur content of the vacuum reside, for example, may be measured by any suitable technique. A preferred technique is laser induced breakdown spectroscopy (LIBS).

Alternatively, or in addition, the measurements may comprise measurements of the vacuum residue after further treatment, for a example after "blowing" of the vacuum residue.

"Blowing" of bitumen feedstock is well known to the person skilled in the art and comprises eating of the bitumen feedstock (in the present invention the vacuum residue) in air, typically under a flowing stream of air, and typically in the temperature range of 250° C. to 350° C., for example, in the range 280° C. to 300° C. This blowing changes the quality of the bitumen to yield a harder, more brittle, bitumen. The bitumen quality may be measured a number of times before and as the product is treated. For example, measurements may be made before blowing, as described above, and then again after blowing and/or the bitumen quality may be measured repeatedly after blowing the product under progressively harsher (e.g. higher temperature) conditions.

In addition, as for conventional bitumen production, a portion of the vacuum residue may be "blown" and mixed back in with a portion of the "unblown" vacuum residue to give a mixed bitumen feedstock. Thus, in the process of the present invention, bitumen quality may be measured on "unblown" vacuum residue, "blown" vacuum residue (optionally after various severities of blowing) or a mixture of portions of "blown" and "unblown" vacuum residues.

This allows blowing conditions to obtain optimum bitumen quality to be determined.

The analytical technique (or techniques) used to determine the bitumen quality is (are) preferably automated, for example performed by a suitable robot or robotic workstation.

The measurements of bitumen quality may be made on all or a portion of the vacuum residue formed in step (iii) of the process of the present invention. Thus, for example, one or more portions of the vacuum residue may be used to measure the bitumen quality and the remainder of the vacuum residue may be further treated to measure coke quality, as described further below.

In a second aspect (step (iv)(b) of the present invention), the coke yield and quality are measured. This is achieved by further heating of the vacuum residue to a temperature in the range 450° C. to 600° C. and measuring the coke quality of the product formed.

In a most preferred ant the asphaltene, stability of the vacuum residue formed in step (iii) is measured prior to sub heating and measurement of the coke quality in step (iv)(b). The asphaltene stability of refinery feedstock vacuum reside has been found to be related to the quality of coke formed from the vacuum residue.

Hence, the measurement of the asphaltene stability of the vacuum reside can enhance the information on the quality of coke formed as measured in step (iv)(b)(ii).

Asphaltenes are polar components of refinery feedstock that are generally soluble in aromatics and insoluble in paraffinic compounds, such as n-alkanes. Thus, if the ratio of paraffinic compounds to aromatic compounds hang for example, if incompatible crude oils are blended together, asphaltenes may precipitate out of solution, and this can cause problems with equipment fouling.

The propensity for this to happen is known as the asphaltene stability.

The coke quality may be determined from the asphaltene stability measurement by applying a suitable model which correlates the asphaltene stability measurement with the coke quality, for example, a model based on previously measured values of coke quality and asphaltene stability.

The measurement of asphaltene stability for crude oils generally is well-known and is described, for example, in ASTM D7060-04 "Standard Test Method for Determination of the Maximum Flocculation Ratio and Peptizing Power in Residual and Heavy Fuel Oils (Optical Detection Method)".

Other industry methods for measurement of asphaltene stability of crude oils are also known, and include, for example, the measurement of xylene equivalents or the measurement of the (Shell) "P" value.

A further method for measurement of asphaltene stability (for blends of two or more hydrocarbon liquids) is described in WO 2004/061450.

A preferred measurement of the asphaltene stability of the vacuum residue for use in the present invention is the critical solvent power of the vacuum residue as defined in WO 2004/061450.

The solvent power of a vacuum residue is a function of the relative ratio of aromatics to saturates therein.

The critical solvent power of the vacuum residue is the solvent power at which asphaltenes precipitate out of the vacuum residue.

As paraffinic hydrocarbon is added to the vacuum residue, the solvent power of the mixture decreases. When the solvent power of the mixture is less than the critical solvent power of the residue precipitation occurs. The more paraffinic compound that has to be added before precipitation occurs, the lower the critical solvent power of the vacuum residue and the greater the stability of the vacuum residue.

Thus, the critical solvent power may be measured by incremental addition of a paraffinic hydrocarbon to the vacuum residue until asphaltenes begin to precipitate.

Alternatively, portions of vacuum residue may be mixed with paraffinic hydrocarbon at different volumes and compositions of paraffinic hydrocarbon and each subjected to vibrational mixing. The asphaltene stability is determined by the onset of precipitation in respective mixtures. The portions of vacuum residue used may be portions of a single vacuum residue obtained from a single sample in step (iii) of the process of the present invention. Alternatively, a plurality of identical samples may be heated in an identical manner in step (iii) to give a plurality of identical vacuum resides, each of which is mixed with a different volume or composition of paraffinic hydrocarbon.

The paraffinic hydrocarbon used is preferably n-heptane.

Other compounds, such as toluene and xylene, may be added with the paraffinic hydrocarbon.

The critical solvent power of the vacuum reside has been found to be related to the propensity of the vacuum residue to form "shot" coke in a refinery coker. In particular, the lower the critical solvent power, the lower the tendency to form shot coke when the vacuum residue is treated in a refinery coker. "Shot" coke is coke in the form of small, spherical particles, although larger particles can also form and/or the particles can agglomerate together. "Shot" coke can cause significant operational issues in delayed coker.

Preferably, the asphaltene stability is measured in an automated manner, for example by means of a robotic won. The onset of precipitation on a addition of the paraffinic hydrocarbon may be determined by any suitable technique, but again this is preferably done in an automated manner, for example using a spectroscopic technique, such as NIR or IR and measuring the change in transmission of radiation. Automated measurement of flocculation can be performed, for example, by the Finnish Measurement Systems Limited PORLA analyzer.

In a further embodiment, where the refinery feedstock is initially heated at atmospheric pressure prior to heating under vacuum in step (iii), the asphaltene stability of the reside formed after heating at atmospheric pressure (atmospheric residue), optionally after being blended with one or more other residues as described above, may also be measured prior to the subsequent heating under vacuum.

In a further embodiment, the sulphur content of the vacuum residues in step (iii) may be measured, as described previously for determination of bitumen quality, such as by using laser induced breakdown spectroscopy (LIBS).

The heating to a temperature in the range 450° C. to 600° C. in step (iv)(b)(i) causes coking of the vacuum residue to produce a "green" coke.

As noted previously, when the coke quality of the vacuum residue is to be measured in step (iv)(b), the vacuum residue formed in step (iii) may be blended with one or more further residues, for example, with a vacuum residue, a solvent deasphalted pitch or a visbroken tar, prior to heating and measurement of the coke quality.

Prior to heating and measurement of the coke quality the vacuum residue may also be blended with further components. Such components may include other hydrocarbons from other pro units within the refinery, such as decant oil or light cycle oil from a fluidized catalytic cracker (CC) unit or hydrocarbons recycled from the coking itself, such as heavy liquids or distillates, as described further below. The components may also include non-hydrocarbon components, such as steam, hydrogen, nitrogen and/or hydrogen sulphide. Addition of hydrogen, for ample, may shift the yields and properties of the products of the coking step.

During coking, cracking of components in the vacuum residue occurs to produce gaseous and liquid products (the liquid products are liquids at room temperature, but with boiling points below the temperature of cracking) which are evolved, and it is the weight loss associated with these components that is thus measured. In a preferred embodiment these gaseous and/or liquid components are themselves analysed. For example, the liquid components may be cooled so the liquid components condense, and subsequently passed to a suitable analysis device, such as by a microanalysis or spectroscopic method to determine sulphur and/or nitrogen content or micro-chromatographic device (for example micro-gas chromatography, micro 2D gas chromatography) to olefin and aromatic content. The distribution of such species throughout the liquid products may also be determined. The gaseous components may also be collected and analysed or may be passed directly to a suitable gas analyser, such as micro-gas chromatography (micro-GC).

All or a portion of the liquid components evolved during coking, such as heavier liquids or distillates, may be separated, recycled and added (for example, by vibrational mixing) to the vacuum residue produced in step (iii), and the mixture subjected to asphaltene stability testing described above and/or subjected to heating in step (iv)(b)(i) described above. This embodiment of the invention simulates coker recycle.

The heating in step (iv)(b)(i) may be performed in a single step, or the vacuum residue may be hated in a series of steps to progressively higher temperatures (partial coking steps). When a series of partial coking steps is performed, the asphaltene stability test and any other tests desired may be applied to the partially coked samples.

The sample may be heated in step (iv)(b)(i) at atmospheric pressure or under vacuum, or a combination thereof. The rate of heating may also be controlled.

In step (iv)(b)(ii) the coke quality of the product formed is measured. The measurements may comprise measurements on the green coke formed in step (iv)(b)(i) itself (i.e. without further treatment) and/or may comprises measurements of the product formed after further treatment, for example after calcination of the green coke to give calcined coke. The green coke may typically be calcine by heating in air to at least 1000° C., typically in the range 1200° C. to 1350° C. The calcination drives off residual hydrocarbons and moisture, and increases the density and physical strength of the coke structure.

A number of techniques may be used which can give information on the coke quality. The coke quality will, at least in part, be determined by the impurities present, typical impurities that it may be desired to measure being sulphur, nickel, vanadium, sodium, iron, calcium, silicon and nitrogen. Suitable techniques for measuring all or some of said impurities include XRF, LIBS or other spectroscopic tools capable of determining the quantities of impurities present.

The coke quality may also be determined in terms of physical properties of the coke formed, such as porosity and vibrated bulk density, volatile material (VM) content and hardness, such as Hardgove Grindability Index, and structure, for example by X-Ray diffraction.

After calcination the coke is also electrically conductive, and this property may also be used to measure the coke quality of the product. Other properties of calcined coke which may be used to determine its quality include air reactivity and $CO_2$ reactivity, which are generally dependent on sulphur content, sodium and calcium content and metals content, coefficient of thermal expansion (CTE) and attritability, and structure by X-Ray diffraction.

The bitumen quality and coke quality may both be measured by performing separate experiments. Alternatively, the bitumen quality and coke quality may both be measured in the same "experiment" by initially heating the sample to a temperature in the range 300° C. to 420° C. and then measuring the bitumen quality of a portion of the vacuum residue formed, and subsequently measuring the coke quality on the remaking vacuum residue as described above. Either or both portions of the vacuum residue may be blended with other residues prior to the respective subsequent treatment as previously described.

The present invention allows the determination of the coke and/or bitumen yield and quality of refinery feedstocks, and blends thereof, allowing optimisation of the blending to enhance the yield and quality of the desired product to be achieved.

In a preferred embodiment of the present invention, once the analysis (analyses) of step (iv) has (have) been performed, suitable refinery process models applied to determine the impact of the refinery feedstocks. Suitable refinery models are known to the person skilled in the art, and may include, for example, linear programme models for feedstock and product evaluation, process optimisation models, such as for refinery-wide optimisation and/or risk-based models, for evaluation of processing impacts of the refinery feedstock.

The process of the present invention will generate a large amount of data on the coke and/or bitumen yield and quality of a plurality of refinery feedstocks. In a further embodiment, this data may be utilised to develop, update and/or verify process suitable models. For example, a large amount of data may be rapidly produced over a broader parameter set than from pilot plant parameter studies enabling the building of a process model, and further data generated may be utilised to provide continuous update and refinement of the process model (for example, for a wider parameter space).

Modelling or other experimental design techniques may be used to generate a set of variable process conditions for the plurality of refinery feedstocks which it is desired to evaluate for the development, updating or verification of one or more process models, and the process of the present invention can be specifically used to evaluate the processes to generate the required data for the process models, such as yield and quality of products from the refinery feedstocks under the defined process conditions.

The invention claimed is:

1. A process for evaluating the coke and/or bitumen yield and quality of a plurality of refinery feedstocks, said process comprising:
   (i) providing a plurality of refinery feedstocks,
   (ii) placing a sample of each of said plurality of refinery feedstocks on a heating device,
   (iii) heating each sample under vacuum to a temperature in the range 300° C. to 420° C. using the respective heating device whilst measuring the weight loss of the sample, and then
   (iv)(a) measuring the bitumen quality of the vacuum residues formed, and/or
   (b)(i) heating the vacuum residues to a temperature in the range 450° C. to 600° C. using the heating device, whilst measuring the weight loss of the sample, and then
      (ii) measuring the coke quality of the products formed.

2. A process as claimed in claim 1 wherein the refinery feedstocks are selected from the group consisting of crude oils, synthetic crudes, biocomponents, visbreaker tars, solvent deasphalted pitches, atmospheric residues, vacuum residues, fuel oils, FCC decant oils and blends of one or more of said components.

3. A process as claimed in claim 1 wherein the heating devices are optical devices or microoscillators.

4. A process as claimed in claim 1 wherein the asphaltene stability of the vacuum residue formed in step (iii) is measured prior to subsequent heating and measurement of the coke quality in step (iv)(b).

5. A process as claimed in claim 1 wherein the plurality of refinery feedstocks comprises at least 20 refinery feedstocks.

6. A process as claimed in claim 5 wherein the plurality of refinery feedstocks comprises at least 50 refinery feedstocks.

7. A process as claimed in claim 1 wherein the vacuum residue formed in step (iii) is blended with one or more other residues prior to step (iv).

8. A process as claimed in claim 7, wherein the vacuum residue formed in step (iii) is blended with a vacuum residue prior to determination of the bitumen quality in step (iv)(a).

9. A process as claimed in claim 7, wherein the vacuum residue formed in step (iii) is blended with a vacuum residue, a solvent deasphalted pitch or a visbroken tar, prior to subsequent heating and measurement of the coke quality in step (iv)(b).

10. A process as claimed in claim 1 wherein the gaseous and/or liquid components evolved during the coking in step (iv)(b)(ii) are themselves analysed.

11. A process as claimed in claim 10 wherein all or a portion of the liquid components evolved during coking may be separated, recycled and added to the vacuum residue produced in step (iii).

* * * * *